(12) United States Patent
Dam et al.

(10) Patent No.: US 8,631,683 B2
(45) Date of Patent: Jan. 21, 2014

(54) DIALYSIS SYSTEMS INCLUDING NON-INVASIVE MULTI-FUNCTION SENSOR SYSTEMS

(75) Inventors: Naim Dam, Muttontown, NY (US); Martin Joseph Crnkovich, Walnut Creek, CA (US); Roland Levin, San Ramon, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 437 days.

(21) Appl. No.: 12/647,820

(22) Filed: Dec. 28, 2009
(Under 37 CFR 1.47)

(65) Prior Publication Data
US 2011/0009800 A1 Jan. 13, 2011

Related U.S. Application Data

(63) Continuation-in-part of application No. 11/903,261, filed on Sep. 21, 2007, now Pat. No. 7,661,294, and a continuation-in-part of application No. 11/703,025, filed on Feb. 6, 2007, now Pat. No. 7,661,293.

(51) Int. Cl.
*G01N 29/024* (2006.01)
*A61M 37/00* (2006.01)
*G01N 29/02* (2006.01)
*G01J 5/28* (2006.01)

(52) U.S. Cl.
USPC ............. 73/19.03; 73/61.75; 73/597; 73/598; 250/343; 604/6.08

(58) Field of Classification Search
USPC ............. 73/19.03, 61.75, 597, 598; 600/6.08; 604/6.08; 250/343
See application file for complete search history.

(56) References Cited

U.S. PATENT DOCUMENTS

| 3,812,482 A | * | 5/1974 | Clark ............................ 340/515 |
| 3,871,913 A | | 3/1975 | Shaldon |
| 3,896,803 A | * | 7/1975 | Mason ............................ 604/32 |
| 3,921,622 A | | 11/1975 | Cole |

(Continued)

FOREIGN PATENT DOCUMENTS

| CN | 1216275 | 5/1999 |
| CN | 1469106 | 1/2004 |

(Continued)

OTHER PUBLICATIONS

Blumenkrantz et al., "Applications of the Redy Sorbent System to Hemodialysis and Peritoneal Dialysis", "Artif Organs" vol. 3, No. 3, pp. 230-236, 1978.*

(Continued)

*Primary Examiner* — Peter Macchiarolo
*Assistant Examiner* — Rose M Miller
(74) *Attorney, Agent, or Firm* — Fish & Richardson P.C.

(57) ABSTRACT

A dialysis system that includes a dialysis machine, a tube connected to the dialysis machine, and a sensor system. The sensor system includes a head having a slot configured to receive the tube and a plurality of sensors secured to the head adjacent the slot. At least one of the plurality of sensors includes a light emitting element configured to transmit light through the tube when the tube is disposed in the slot and a light receiving element configured to receive the light emitted by the light emitting element after the light passes trough the tube.

30 Claims, 8 Drawing Sheets

(56) References Cited

U.S. PATENT DOCUMENTS

| | | |
|---|---|---|
| 3,935,876 A * | 2/1976 | Massie et al. ............... 137/177 |
| 4,068,521 A | 1/1978 | Cosentino et al. |
| 4,174,231 A | 11/1979 | Hobgood |
| 4,191,351 A | 3/1980 | Goyne |
| 4,341,116 A | 7/1982 | Bilstad et al. |
| 4,581,141 A | 4/1986 | Ash |
| 4,666,598 A | 5/1987 | Heath et al. |
| 4,684,460 A | 8/1987 | Issautier |
| 4,728,496 A | 3/1988 | Petersen et al. |
| 4,730,493 A | 3/1988 | Lebaud et al. |
| 4,770,787 A | 9/1988 | Heath et al. |
| 4,784,495 A | 11/1988 | Jonsson et al. |
| 4,789,467 A | 12/1988 | Lindsay et al. |
| 4,797,655 A | 1/1989 | Orndal et al. |
| 4,909,786 A | 3/1990 | Gijselhart et al. |
| 4,966,579 A | 10/1990 | Polaschegg ............... 604/65 |
| 4,981,467 A | 1/1991 | Bobo, Jr. et al. ............... 604/65 |
| 4,997,577 A | 3/1991 | Stewart |
| 5,064,412 A | 11/1991 | Henke et al. |
| 5,102,392 A | 4/1992 | Sakai et al. ............... 604/122 |
| 5,176,631 A | 1/1993 | Koenig ............... 604/65 |
| 5,179,862 A | 1/1993 | Lynnworth |
| 5,211,201 A | 5/1993 | Kamen et al. ............... 137/1 |
| 5,256,371 A | 10/1993 | Pippert |
| 5,262,068 A | 11/1993 | Bowers et al. |
| 5,277,820 A | 1/1994 | Ash |
| 5,304,349 A | 4/1994 | Polaschegg |
| 5,392,638 A | 2/1995 | Kawahara |
| 5,394,732 A | 3/1995 | Johnson et al. |
| 5,409,612 A | 4/1995 | Maltais et al. |
| 5,421,813 A | 6/1995 | Ohnishi |
| 5,453,576 A | 9/1995 | Krivitski |
| 5,496,273 A | 3/1996 | Pastrone et al. ............... 604/67 |
| 5,536,412 A | 7/1996 | Ash |
| 5,589,070 A | 12/1996 | Maltais et al. |
| 5,591,344 A | 1/1997 | Kenley et al. |
| 5,603,902 A | 2/1997 | Maltais et al. |
| 5,605,630 A | 2/1997 | Shibata |
| 5,641,892 A | 6/1997 | Larkins et al. ............... 73/19.03 |
| 5,644,402 A * | 7/1997 | Chevallet ............... 356/440 |
| 5,685,989 A | 11/1997 | Krivitski et al. |
| 5,713,125 A | 2/1998 | Watanabe et al. |
| 5,755,563 A | 5/1998 | Clegg et al. ............... 417/326 |
| 5,788,099 A | 8/1998 | Treu et al. |
| 5,830,365 A | 11/1998 | Schneditz |
| 5,919,369 A | 7/1999 | Ash |
| 5,935,099 A | 8/1999 | Peterson et al. ............... 604/65 |
| 5,944,684 A | 8/1999 | Roberts et al. |
| 6,000,567 A | 12/1999 | Carlsson et al. |
| 6,036,858 A | 3/2000 | Carlsson et al. |
| 6,085,574 A | 7/2000 | Neftel et al. |
| 6,086,753 A | 7/2000 | Ericson et al. |
| 6,142,008 A | 11/2000 | Cole et al. |
| 6,143,181 A | 11/2000 | Falkvall et al. |
| 6,170,785 B1 | 1/2001 | Lampropoulos |
| 6,190,855 B1 | 2/2001 | Herman et al. |
| 6,277,277 B1 | 8/2001 | Jacobi et al. |
| 6,280,632 B1 | 8/2001 | Polaschegg |
| 6,308,721 B1 | 10/2001 | Bock et al. |
| 6,409,699 B1 | 6/2002 | Ash |
| 6,416,293 B1 | 7/2002 | Bouchard et al. |
| 6,428,706 B1 | 8/2002 | Rosenqvist et al. |
| 6,515,487 B1 | 2/2003 | Dawson et al. |
| 6,542,761 B1 | 4/2003 | Jahn et al. |
| 6,622,542 B2 | 9/2003 | Derek et al. |
| 6,731,971 B2 | 5/2004 | Evans, III et al. ............... 600/431 |
| 6,755,976 B2 | 6/2004 | Rosenqvist et al. |
| 6,796,195 B2 | 9/2004 | Povey et al. |
| 6,821,432 B2 | 11/2004 | Metzner |
| 6,878,283 B2 | 4/2005 | Thompson |
| 7,033,498 B2 | 4/2006 | Wong |
| 7,047,809 B2 | 5/2006 | Cobb |
| 7,077,956 B2 | 7/2006 | Rovatti |
| 7,241,272 B2 | 7/2007 | Karoor et al. |
| 7,243,541 B1 | 7/2007 | Bey et al. |
| 7,481,114 B2 | 1/2009 | Lynnworth |
| 7,661,293 B2 | 2/2010 | Dam |
| 7,661,294 B2 | 2/2010 | Dam |
| 7,947,179 B2 | 5/2011 | Rosenbaum et al. |
| 8,110,104 B2 | 2/2012 | Crnkovich et al. |
| 2002/0079695 A1 | 6/2002 | Campbell et al. |
| 2003/0105424 A1 | 6/2003 | Karoor et al. |
| 2004/0019312 A1 | 1/2004 | Childers |
| 2004/0050789 A1 | 3/2004 | Ash |
| 2005/0274658 A1 | 12/2005 | Rosenbaum et al. |
| 2006/0052963 A1 | 3/2006 | Shkarlet |
| 2006/0277977 A1 | 12/2006 | Kahn et al. |
| 2007/0093160 A1 | 4/2007 | Collins |
| 2007/0158247 A1 | 7/2007 | Carr et al. |
| 2007/0158249 A1 | 7/2007 | Ash |
| 2007/0158268 A1 | 7/2007 | DeComo |
| 2007/0161113 A1 | 7/2007 | Ash |
| 2007/0161941 A1 | 7/2007 | Ash et al. |
| 2007/0181499 A1 | 8/2007 | Roberts et al. |
| 2007/0235376 A1 * | 10/2007 | Daniel ............... 210/138 |
| 2008/0098798 A1 | 5/2008 | Riley et al. |
| 2008/0145249 A1 * | 6/2008 | Smisson et al. ............... 417/474 |
| 2008/0146996 A1 * | 6/2008 | Smisson et al. ............... 604/67 |
| 2008/0149563 A1 | 6/2008 | Ash |
| 2008/0156476 A1 * | 7/2008 | Smisson et al. ............... 165/185 |
| 2008/0177216 A1 | 7/2008 | Ash |
| 2008/0195060 A1 * | 8/2008 | Roger et al. ............... 604/246 |
| 2009/0078047 A1 | 3/2009 | Dam |
| 2009/0114595 A1 | 5/2009 | Wallenas et al. |

FOREIGN PATENT DOCUMENTS

| | | |
|---|---|---|
| CN | 1469106 A * | 1/2004 |
| EP | 0 278 100 | 8/1988 |
| EP | 446605 A1 | 9/1991 |
| EP | 0 673 658 | 9/1995 |
| EP | 0813041 | 12/1997 |
| EP | 1 342 480 | 9/2003 |
| JP | 4158258 | 6/1992 |
| JP | 4505412 A | 9/1992 |
| JP | 9178712 | 7/1997 |
| JP | 2002-333434 | 11/2002 |
| JP | 2003-043017 | 2/2003 |
| JP | 2002131288 A | 5/2005 |
| JP | 2005134228 A | 5/2005 |
| KR | 0157986 | 11/1998 |
| KR | 10-2002-0063001 | 7/2002 |
| KR | 2003-0035584 | 5/2003 |
| KR | 1020030035584 A | 5/2003 |
| KR | 2003-0097746 | 12/2003 |
| KR | 10-0516727 | 9/2005 |
| WO | WO 96/40322 | 12/1996 |
| WO | WO 98/17333 | 4/1998 |
| WO | WO 99/37342 | 7/1999 |
| WO | WO 01/92867 A1 | 12/2001 |
| WO | WO 02/30267 | 4/2002 |
| WO | WO 02/43859 | 6/2002 |
| WO | WO 03/040702 | 5/2003 |
| WO | WO 2005/111602 | 11/2005 |
| WO | WO 2005/123230 | 12/2005 |
| WO | WO 2007/028056 | 3/2007 |
| WO | WO 2007/081383 | 7/2007 |
| WO | WO 2007/081384 | 7/2007 |
| WO | WO 2007/081565 | 7/2007 |
| WO | WO 2007/081576 | 7/2007 |
| WO | WO 2009/042061 | 4/2009 |
| WO | WO 2012/006425 | 1/2012 |

OTHER PUBLICATIONS

"RX Guide to Custom Dialysis," COBE Renal Care Inc., Revision E. Sep. 1993.

"Sorbent Dialysis Pimer," COBE Renal Care, Inc., Sep. 4, 1993 Ed.

Operator's Manual—Fresenius 2008K Hemodialysis Machine (2000).

Observations by third party under Article 115 EPC against patentability of European Patent Application No. 08833649.0.

* cited by examiner

DIALYSIS SYSTEMS INCLUDING NON-INVASIVE MULTI-FUNCTION SENSOR SYSTEMS

CROSS-REFERENCE TO RELATED APPLICATIONS

This application is a continuation-in-part application of and claims priority to U.S. application Ser. No. 11/903,261, filed on Sep. 21, 2007 now U.S. Pat. No. 7,661,294, which is incorporated by reference herein. This application is also a continuation-in-part application of and claims priority to U.S. application Ser. No. 11/703,025, filed on Feb. 6, 2007 now U.S. Pat. No. 7,661,293, which is incorporated by reference herein.

TECHNICAL FIELD

The present invention is directed to dialysis systems including non-invasive multi-function sensor systems.

BACKGROUND

In certain applications in medical equipment such as kidney dialysis machines, infusion pump blood analyzers, transfusion systems, cardio-pulmonary bypass machines and the like, an attempt is made to ensure patient safety. In these applications flexible plastic tubes are used for tasks such as to supply the patient with medication, supply saline solution, extract fluid such as blood from the patient's body and supply it back after cleansing or purification, as well as for other functions. For example, during a kidney dialysis process tubes are connected to both the vein and artery of the patient for the blood extraction and return after cleansing. Another tube is used for infusion of medicine.

For each tube connected to the patient's body it is desirable and even necessary to monitor different conditions relative to the liquid flowing in the tube and even conditions concerning the tube itself. For example, it might be required or desirable to sense the temperature of the liquid flowing in the tube, sense the presence of air bubbles and/or particles present in the liquid and to characterize these as to size and quantity. Sensing of other conditions include that of the type of liquid, such as blood or a clear saline solution, flowing in the tube as well as sensing an occlusion in the flow. It is even desirable to sense that a required tube is connected to the patient.

In the prior art, a separate sensor and an associated electronic circuit is used to perform each of the sensing functions. This complicates the use of the medical equipment in that each of the sensors has to be mounted to the one or more tubes. For example, several different sensors are separately mounted to a single tube to sense conditions that are supposed to be monitored relative to the liquid flowing in that tube. This requires a selection process by the medical technician. It also makes use of the medical equipment more cumbersome in terms of operation, size and also makes it more costly. Also, since a different sensor and its associated electronic circuit is required to monitor each of the different conditions, the reliability of the entire system of the medical equipment and sensors decreases because the failure mode possibility increases due to the use of multiple and separate sensors each having a dedicated electronic circuit. Further, the user of the equipment often needs to coordinate with multiple vendors to purchase different sensors and different electronic circuits for different functionality. Accordingly, a need exists for apparatus that can overcome these problems and disadvantages.

SUMMARY

In general, this invention relates to dialysis systems including non-invasive multi-function sensor systems.

One aspect of the invention provides a dialysis system that includes a dialysis machine, a tube connected to the dialysis machine, and a sensor system. The sensor system includes a head having a slot configured to receive the tube and a plurality of sensors secured to the head adjacent the slot. At least one of the plurality of sensors includes a light emitting element configured to transmit light through the tube when the tube is disposed in the slot and a light receiving element configured to receive the light emitted by the light emitting element after the light passes trough the tube.

Another aspect of the invention features a dialysis system that includes a dialysis machine, a tube connected to the dialysis machine, and a sensor system. The sensor system includes a head having a slot configured to receive the tube, and a plurality of sensors secured to the head adjacent the slot. At least one of the plurality of sensors includes an infrared temperature sensor element configured to project infrared energy into the tube when the tube is disposed in the slot.

Another aspect of the invention provides a system that can perform a plurality of sensing functions and that includes an integrated multifunction sensing module. In this aspect of the invention, the module has a head that has a slot into which the tube is to be placed. The head incorporates a plurality of sensors such as those needed for air bubble detection, temperature sensing and pressure sensing for use in sensing occlusions in the fluid flow in the tube and also to give an indication of the tube being positively connected to the head. The head also includes a light emitting device, such as an LED, that transmits a light beam into the tube in the slot and a photodetector that receives the light. This permits a determination of whether the fluid in the tube is blood or a more clear liquid, such as saline solution or a flow of medicament.

Implementations may include one or more of the following features.

In some implementations, the tube includes a plurality of tubular segments connected together.

In certain implementations, the tube is connected to a patient in a manner such that fluid can be drawn from the patient via the tube.

In some implementations, the tube is connected to a patient in a manner such that fluid can be delivered to the patient via the tube.

In certain implementations, the sensor system also includes a liquid type detection circuit responsive to the light received by the light receiving element to determine the color of fluid in the tube.

In some implementations, the liquid type detection circuit also operates to determine whether the tube is present in the slot.

In certain implementations, the liquid type detection circuit also operates to determine whether liquid is in the tube.

In some implementations, the sensor system also includes a multiplexer controlled by timing signals to separately actuate the liquid type circuit and a circuit associated with at least one of the other sensors.

In certain implementations, at least one of the plurality of sensors includes a first piezoelectric element mounted on a first wall of the head adjacent the slot, and a second piezoelectric element mounted on a second wall of the head adjacent the slot. The second wall is opposite the first wall.

In some implementations, the tube is disposed in the slot of the head, and the first piezoelectric element and the second piezoelectric element are positioned outside of the tube and are configured to detect an air bubble in fluid in the tube.

In certain implementations, the sensor system also includes an air bubble detection circuit to supply ultrasonic energy to one of the piezoelectric sensor elements, to receive the ultrasonic energy transmitted through the tube by the other of the piezoelectric sensor elements, and to determine from the received energy whether an air bubble is present in fluid in the tube.

In some implementations, at least one of the plurality of sensors includes an infrared temperature sensor element configured to project infrared energy into the tube when the tube is disposed in the slot, and at least one of the plurality of sensors includes a light emitting element configured to transmit light through the tube when the tube is disposed in the slot, and a light receiving element configured to receive the light emitted by the light emitting element after the light passes trough the tube.

In certain implementations, the sensor system also includes a temperature sensing circuit responsive to infrared energy sensed by the infrared temperature sensor element to determine the temperature of fluid in the tube.

In some implementations, at least one of the plurality of sensors is a force sensor.

In certain implementations, the sensor system also includes a force detection circuit to determine a force applied to the force sensor by the tube.

In some implementations, the force detection circuit is configured to determine whether the tube is present in the slot.

In certain implementations, the force detection circuit is configured to determine an internal pressure of the tube.

In some implementations, the force sensor contacts an outer surface of the tube when the tube is disposed in the slot.

In certain implementations, walls of the head adjacent the slot define recesses in which the plurality of sensors are disposed.

In some implementations, the walls of the head further define passages extending from the recesses to outer surfaces of the walls, and wires connected to the sensors extend through the passages to a location external the head.

In certain implementations, the slot has a width that is less than a width of the tube when the tube is undeformed.

In some implementations, the head of the sensor system is made of a transparent plastic material.

In certain implementations, the dialysis machine includes a display.

In some implementations, the dialysis machine is a hemodialysis machine.

In certain implementations, the dialysis system also includes a microprocessor in communication with the sensors.

In some implementations, the microprocessor is configured to produce outputs to one or more other devices, such as a display device, a printer, an audio alarm, an RS 232 output, and/or a blood pump, based on signals received from the sensors.

In certain implementations, the microprocessor is configured to activate an alarm (e.g., a visual or audible alarm) and/or control operation of a blood pump based on signals from the sensors indicating a presence of liquid within the tube.

In some implementations, the microprocessor is configured to activate an alarm and/or inhibit operation of a blood pump based on signals from the sensors indicating an occlusion in a flow of liquid within the tube.

In certain implementations, the microprocessor is configured to activate an alarm and/or control operation of a blood pump based on signals from the sensors indicating whether or not the tube is present within the slot.

In some implementations, the microprocessor is configured to activate an alarm and/or inhibit operation of a blood pump based on signals from the sensors indicating a presence of air bubbles in a flow of liquid within the tube.

In certain implementations, the dialysis system also includes a display device in communication with the microprocessor, and the microprocessor is configured to drive the display device to display measurement results and/or warnings based on signals received from the sensors.

In some implementations, the dialysis system also includes a blood pump in communication with the microprocessor, and the microprocessor is configured to control operation of the blood pump based on signals received from the sensors.

In certain implementations, the head is formed of a block of material, such as a clear polycarbonate plastic, that has a slot with opposing side walls on which the various sensor elements are mounted.

In some implementations, the tube is laid in the slot and is contacted by those of the sensors that need physical contact to perform its function.

In certain implementations, leads from the various sensors mounted in the head are connected to an electronic circuit that includes a microprocessor that is programmed to perform the various functions related to the sensors mounted in the head.

In some implementations, the electronic circuit includes a multiplexer so that a single microprocessor can be used to control all sensing functions.

Other aspects, features, and advantages of the present invention will become more apparent upon reference to the following specification and drawings.

DETAILED DESCRIPTION

Figure 1:
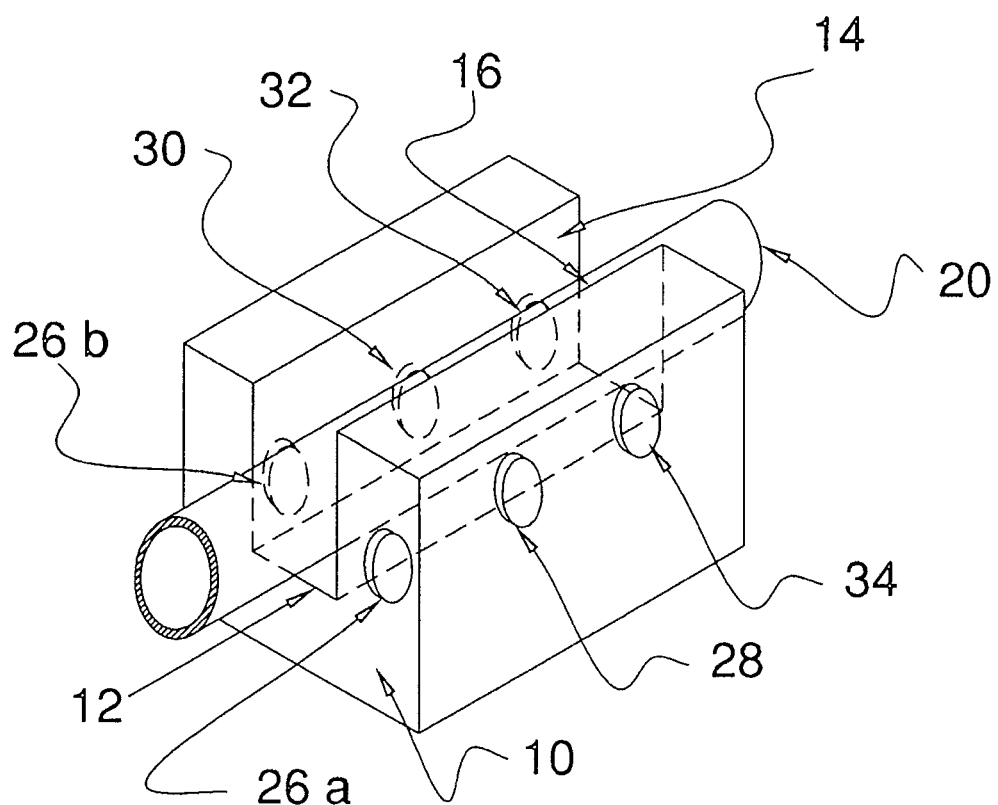
FIG. 1 is a perspective view of the integral multi-function sensor head.
Figure 2:
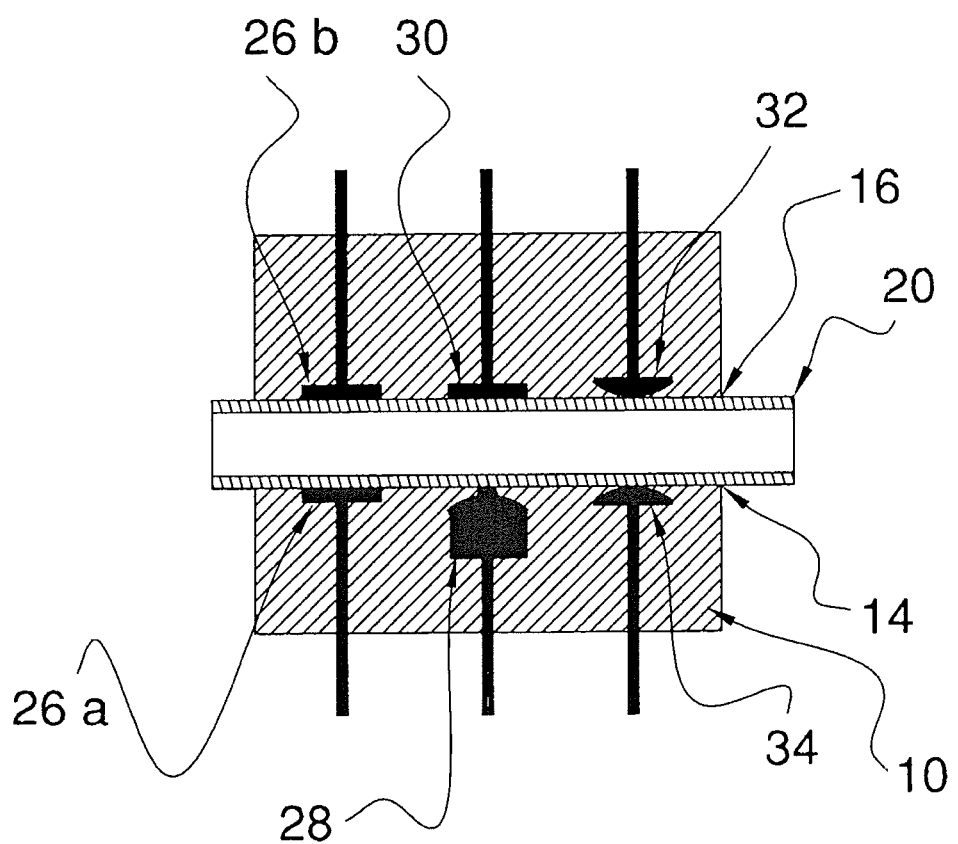
FIG. 2 is a cross section of the head of FIG. 1.

Referring to FIGS. 1 and 2, an integral multi-function sensor has a head 10 that is a block of a plastic material such as UDEL polysulfone resin manufactured by Solvay Advanced Polymers. The head 10 is illustratively shown as being a generally rectangular shape and can be molded by any suitable technique. In the head 10 there is a longitudinal slot 12 that has opposing side walls 14 and 16. A tube 20 of flexible and elastically outwardly expansible plastic material having a liquid flowing in it is to be placed in the slot 12. The tube 20 is to have one end connected to the body of a patient and the other end connected to a liquid supply, such as a medicine or saline solution, or to a machine such as a dialysis machine. In the molding of the head 10 a number of depressions are formed in the opposing slot side walls 14 and 16. Different types of sensor elements, to be described below, are mounted in the depressions and each depression is of a shape to accommodate the particular type of sensor element that is to be mounted in it. The slot side wall thickness is typically 0.30" to 0.050" depending upon plastic material and the sensor elements used. A hole is drilled through the outside wall of the head 10 to each of the depressions in the slot sidewall 14 and 16 to accommodate a respective lead wire or wires connected to the respective sensor element.

Considering the sensor elements, near one end of the head 10 is a pair of piezoelectric elements 26a and 26b mounted opposing each other in the slot opposing slot side walls 14 and 16. Near the center of the head 10 a temperature sensor 28 is mounted in one of the slot side walls 14 and a force sensor 30 is mounted in the other sidewall 16. Near the other end of the head 10 a light emitting element 32, such as an LED, is mounted in the side wall 14 and a photodetector 34 is mounted opposing it in the side wall 16. The representation of the shapes of the various sensor elements are in schematic form and the shape will depend upon the specific sensor element that is used. The placement of the various sensor elements also can be varied. Each of the sensor elements is held in its respective depressions by a suitable adhesive, such as an epoxy, and the lead wires for each sensor element pass out through the walls of the head that form the slot to be exterior of the head so as to be able to be connected to an electronic circuit, to be described below.

In the operation of the system, the plastic tube 12 is laid in the slot 12 of the head 10. The width of the slot 12 is slightly less than the outer diameter of the plastic tube 20 so that the faces of the sensor elements 26, 28 and 30 mounted in the opposing slot side walls 14 and 16 that need to be in contact with the tube 20 makes such contact. A typical deformation or squeeze of the tube in the slot would be 15% to 20% of the tube outer diameter. The light emitting element 32 and photo transistor 34 optical elements need not necessarily make contact with the wall of the plastic tube but one or both of these elements can make such contact. A description of individual sensor elements and their respective functions follows.

The piezoelectric elements 26a and 26b are of any suitable material used in ultrasonic technology, such as PZT or PVDF material. In the integral multi-function sensor system, the piezoelectric elements 26a and 26b operate as part of an air bubble detection and characterization apparatus. In such an apparatus, ultrasonic energy is supplied to one of the piezoelectric elements 26 and is transmitted though the tube 20 to be received by the other element. A circuit of this type is described in U.S. patent application Ser. No. 11/703,025, filed Feb. 7, 2007 for "Ultrasonic System for Detecting and Quantifying of Air Bubbles/particles in a Flowing Liquid", which is assigned to the assignee of this application and whose disclosure is incorporated herein by reference. This system is briefly described below with reference to FIG. 3. Other ultrasonic type systems also can be used to detect air bubbles.

The temperature sensor element 28, in some implementations, is an infrared thermocouple, an example being P/N: 150042, Model No C UIRT-K-98.6f/37C manufactured by Exergen, Watertown, Mass. This device has the ability to measure the internal temperature of the liquid in the tube 20 non-invasively by measuring both tube surface temperature and the ambient temperature. It is preferred that the sensor element 28 is mounted in the head 10 so as to converge the sensor infrared beam at a focus point in the middle of tube 20 to measure fluid temperature accurately.

Figure 5:
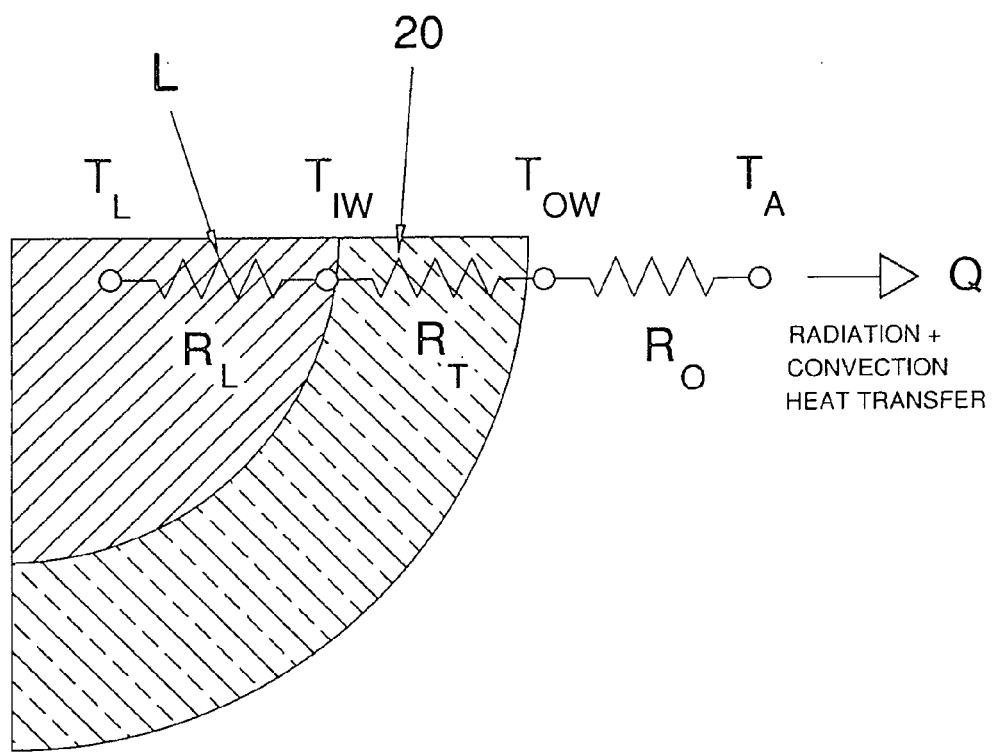
FIG. 5 is a view that explains operation of the infrared sensor used to measure temperature of a liquid in the tube.

The operation of the temperature sensor element 28 is described referring to FIG. 5. As seen in FIG. 5, a liquid L flowing in a tube such as the tube 20 having a temperature $T_L$ which is represented by thermal resistance $R_L$ transfers heat by conduction to the tube inside surface $T_{IW}$, which in turn conducts heat to the tube external surface $T_{OW}$. This transfer is represented by the thermal resistance $R_T$. The heat on the tube outer wall is transferred to the environment via radiation and convection as represented by thermal resistance Ro. Using the method of thermal analysis with electrical analogs: current=heat flow and voltage=temperature, the heat transfer equation may be written as follows:

$$Q = \frac{1}{R_L + R_T + R_O}(T_L - T_A)$$

where

Q=Heat transfer, and $R_L+R_T=R_O$

For heat balance:

$$Q = \frac{1}{R_O}(T_{OW} - T_A)$$

Accordingly, $$T_L = \frac{R_L + R_T + R_O}{R_o}(T_{OW} - T_A) + T_A$$

The infrared sensor 28 measures both $T_{OW}$ and $T_A$. The output lead of sensor 28 is connected to a suitable circuit that includes an analog to digital converter and other necessary circuit for converting the change in temperature measured by the sensor 28 into a digital value and a suitably programmed microprocessor or similar device to automatically solve the equation for the liquid temperature $T_L$. The technique used has been found to be able to measure the liquid temperature with an accuracy of ±0.2° C. The measurement is done non-invasively and provides a highly accurate method of monitoring the temperature of interest. The measured value of the liquid temperature can be used for control purposes, such as turning on and off heating and cooling units or to advise the system operator of changes in temperature.

Figure 4:
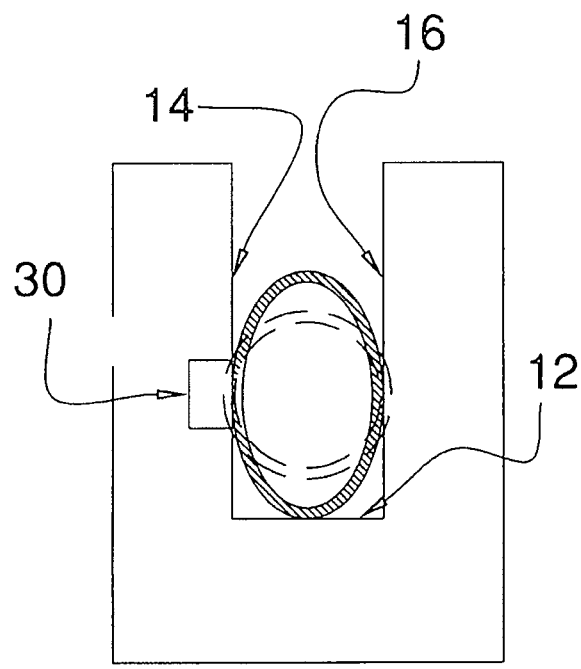
FIG. 4 is a cross-sectional view showing tube deformation.

Sensor element 30 is a force/pressure sensor that accomplishes non-invasive measurement of the internal pressure of the elastic tube 20. During dialysis or infusion of a medicine, the internal pressure of the liquid in the tube 20 exerts force on the inner wall of the tube which is transmitted to the tube outside wall. The force exerted on the tube outer wall has a linear relationship with the tube internal pressure. As shown in FIG. 4, a tube 20 placed in the slot 12 with no liquid flowing in it has a somewhat elliptical shape. Liquid flowing through the tube causes it to expand to a more circular shape a shown by the dash lines. The outer tube wall expansion is measured using a force or strain gauge pressure sensor 30. A suitable force sensor element is P/N: DEL 2239 equivalent and manufactured by Strain Measurement Device, Meriden Conn. The face of the sensor element 30 contacts the outer wall of the tube laid in the slot 12. Such force or strain gauge devices produce a change in resistance as a measurement of the force sensed.

The force sensor 30 is used to perform several functions. It detects an occlusion in the tube by sensing a sudden change in pressure of the liquid in the tube 20. There also will be drop in pressure in the case of a pump failure occurs. The sensor 30 also detects the presence of a tube in sensing slot 12. That is, insertion of the tube 20 in the slot 12 exerts a force against the sensor element 30. The sensor 30 differentiates between dry and liquid presence conditions in the tube. That is, when liquid flows in the tube 20 the force on the tube outer wall will be greater than if there is no liquid flowing in the tube.

The sensor elements 32 and 34 provide for detection of the type of liquid flowing in the tube 20. A typical use would be in detecting if there is blood, or a similar dark liquid, or a clear liquid, or a saline solution, which is relatively clear. Another use is to detect if there is any liquid in the tube or if it is dry. The light emitting element 32 is a suitable device, such as an Infrared emitting diode, and the light receiving element 34 a suitable device, such as a silicon photo transistor. The light emitting element 32, which can be an infrared energy emitting diode, is positioned so as to have its output beam focused in the center of the tube 20. A constant current source is used to drive infrared emitting diode. The photo transistor 34 receives the light energy transmitted through the tube 20. The optical transmission through the tube and a liquid flowing through it is amplified and an amplified analog signal is digitized and analyzed by a microprocessor, as described below.

The optical elements 32 and 34 accomplish a number of functions. There is a detection of blood vs. saline solution since the amount of light passing through the liquid will be of different amplitudes. Different amplitudes of light will be detected by the detector 34 when there is no tube in the slot, tube with a clear liquid flowing in it, and a tube with blood inside the tube. All of these different conditions can be recognized and different indications given to the operator of the equipment.

In certain applications it is important to detect presence of a tube in the slot before fluid is injected. By combining the pressure and optical sensing techniques described above, the system provides added reliability to sense tube presence or absent conditions.

Figure 3:
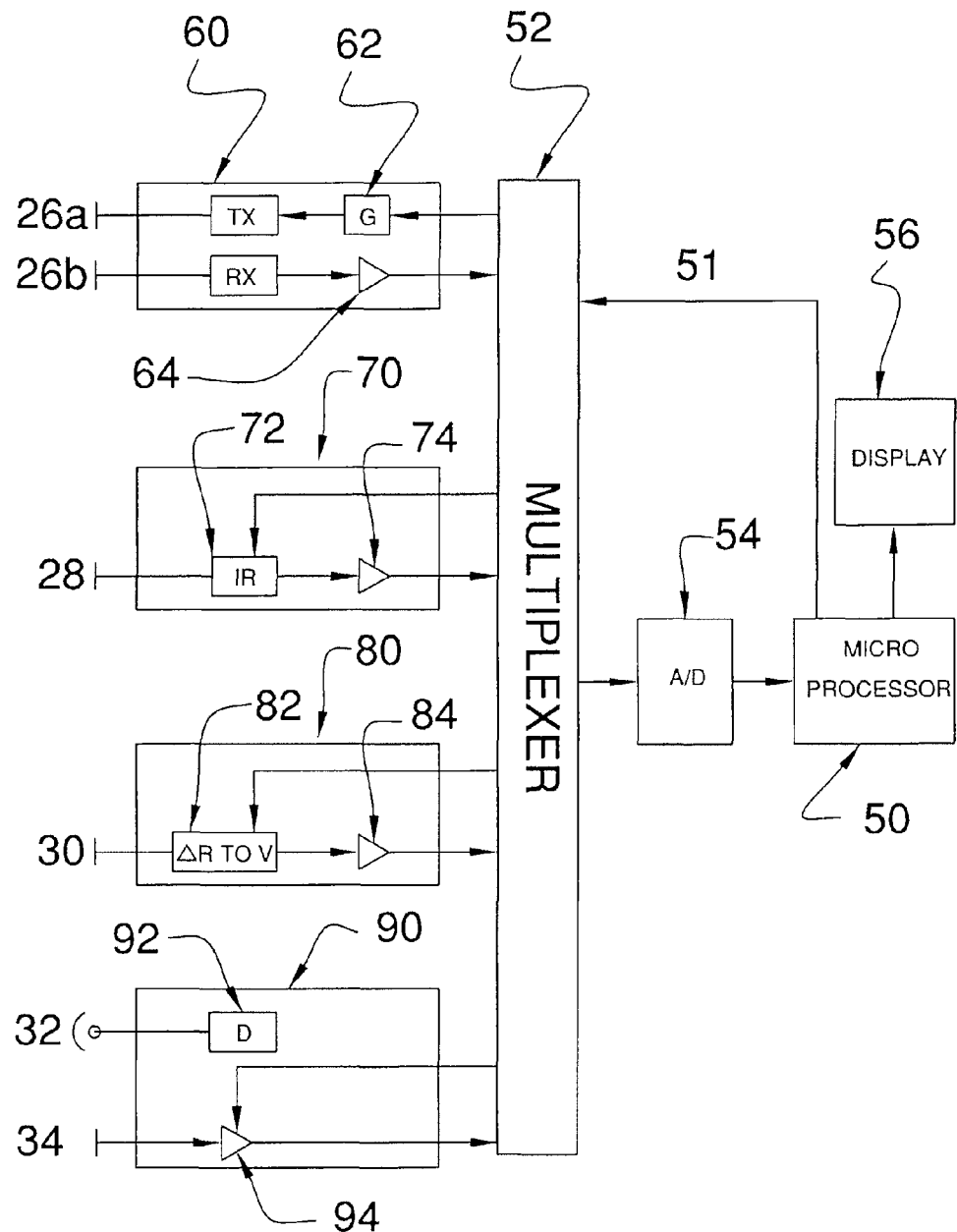
FIG. 3 is a block diagram of the electronic circuit of the system.

FIG. 3 is a block diagram of an electronic circuit that can be used with the multi-function sensor. The circuit of FIG. 3 is integral in that one microprocessor is used to control all of the measuring functions for all of the sensors mounted in the head. While this is generally preferred, other circuits can be used, for example, a separate circuit with its own microprocessor and display for each different type of sensor. Also, it is not necessary to utilize all of the sensor elements of the head 10. For example, in a particular use, it might not be necessary to measure one of the conditions measured by one of the sensor elements.

Referring to FIG. 3, there is a microprocessor 50 that is suitably programmed to perform all of the functions described below. That is, the microprocessor 50 outputs the necessary signals to control the operation of each of the several sensor elements to perform its intended function and to produce an output measurement. The microprocessor 50 also has an output on line 51 that controls operation of a bi-directional multiplexer 52 that is gated by the microprocessor to sequentially apply the signals from the microprocessor 50 to control operation of an air bubble detection and characterization circuit 60 associated with the piezoelectric sensor elements 26a and 26b, a temperature sensing circuit 70 associated with sensor element 28, a pressure sensing circuit 80 associated with the force sensor 30, and a liquid detection circuit 90 associated with the optical elements 32 and 34. An analog to digital converter 54 digitizes an analog output signal from any of the circuits 60, 70, 80 and 90 and applies it to the microprocessor 50 for processing for producing the proper output depending upon the sensor element that is active. The microprocessor 50 drives a visual display device 56 to display measurement results, warnings, and other information. The microprocessor also can produce outputs to other devices such as printers, audio alarms, RS 232 output, etc.

The air bubble and particle sensing circuit 60 is gated on for operation by the multiplexer 52 for a predetermined time by the microprocessor 50. Considering the air bubble detection and characterization circuit 60, as described in the aforesaid patent application Ser. No. 11/703,025, energy in the ultrasonic frequency range, for example 2-5 MHz, is supplied by a generator 62 to the element 26a or 26b that is to be the transmitter element to be transmitted to the opposing other element which serves as a receiver element. The received ultrasonic energy is amplified in an amplifier 64 and detected and preferably split by a suitable circuit into a steady state (DC) component and a varying or transient (AC) component, the components respectively being indicative of the absence and the presence of an air bubble or a particle in the liquid. The two components of the signal are applied to the A/D converter 56 whose output is supplied to microprocessor 50 which uses the digital data that corresponds to the presence of a varying transient component to indicate the presence of an air bubble and/or a particle and to determine its characteristics. When liquid is flowing through the tube 20 the presence of the steady-state component indicates that the system is operating properly to provide a continuous self check against system malfunction.

The temperature sensing circuit 70 is any suitable conventional circuit used to measure temperature based on infrared (IR) energy. Such circuits are well known in the art. When gated on by the microprocessor 50 through the multiplexer 52, the temperature sensing circuit 70 electronics 72 produces the IR beam of energy that heats the wall of the tube 20 in the manner described with respect to FIG. 5 and produces an analog output voltage that is amplified by an amplifier 74. The analog output is applied to the analog to digital converter 54 and the digital output applied to the microprocessor for processing and display.

The force sensing circuit 80 that uses the sensor element 30 has a circuit, such as a bridge circuit, that converts the change of resistance of the sensor element in response to the force or pressure into a voltage that is applied to an amplifier 84 and then through the multiplexer 52 to the analog to digital converter 54. The measured force represented by the analog voltage is converted into digital format to be used by the microprocessor 50 and to be displayed on the display 56.

The liquid color sensing circuit 90 has a drive circuit 92 for the light emitting element 92 which preferably is left on at all times when the system is operating. An amplifier 94 that is gated on by signals from the microprocessor 50 permits the signal generated from the light passing through the tube 20 and/or liquid that is received by the photo transistor 34 to pass through the multiplexer 52 to the analog to digital converter 54. As explained above, the amplitude of the signal produced by the photo transistor corresponds to the absence of liquid in the tube and the color of the liquid. After processing of the digital signal by the microprocessor the results are displayed on the display 56.

The integral multi-function sensor can be employed as a component of an extracorporeal fluid circuit used in filtering blood from a patient during hemodialysis. In this regard, the integral multi-function sensor can be used to monitor different conditions relative to liquid flowing within the extracorporeal fluid circuit.

Figure 6:
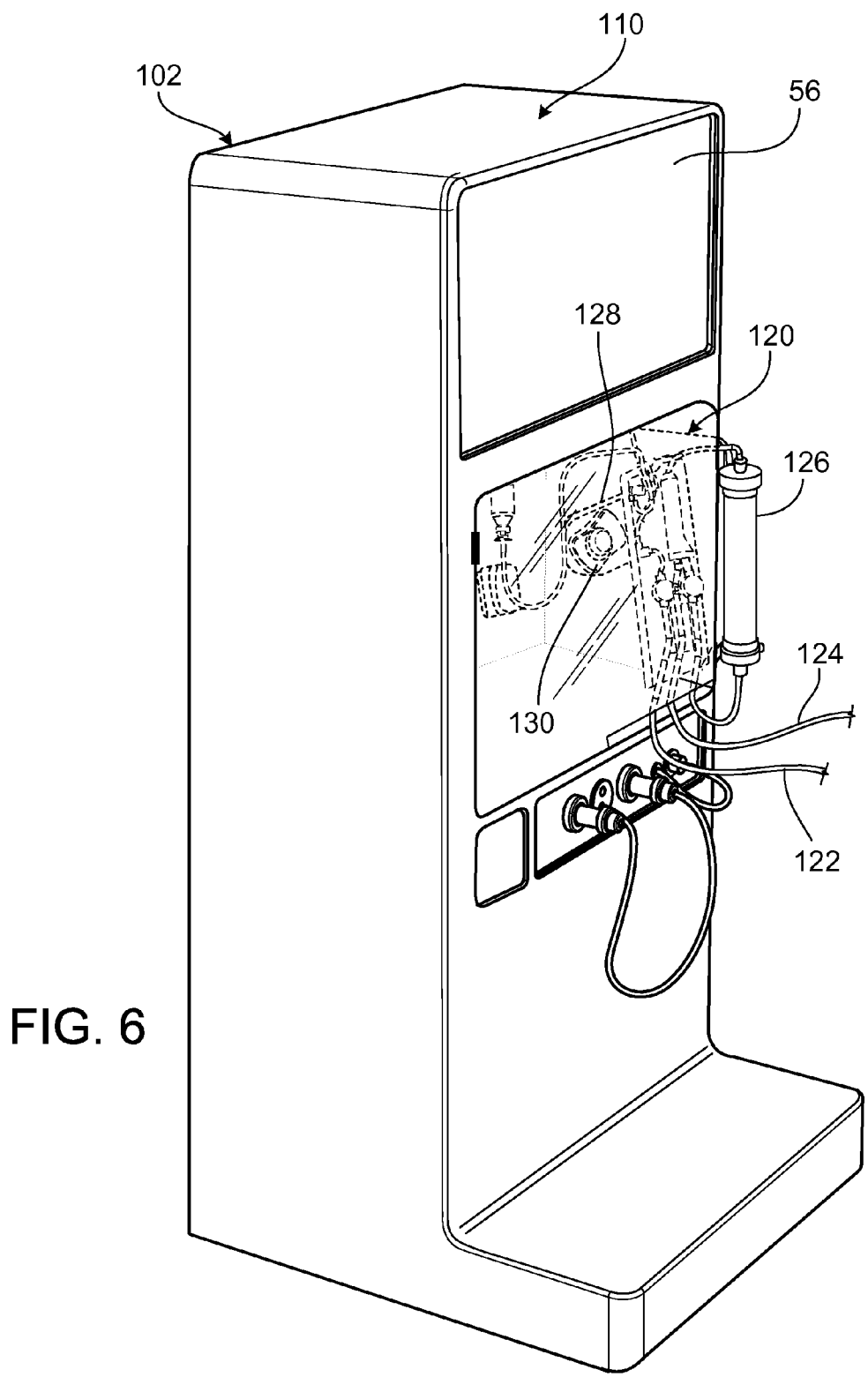
FIG. 6 is a perspective view of a hemodialysis system.

For example, FIG. 6 shows a hemodialysis system 100 that includes a hemodialysis machine 110 that incorporates the integral multi-function sensor as a component part of an associated blood component set 120. The blood component set 120 is secured to a front face of the hemodialysis machine 110. The blood component set 120 includes arterial and venous patient lines 122, 124 that are connected to a patient during treatment. The arterial patient line 122 is connected to an inlet port of a dialyzer 126 via a series of blood lines, and the venous patient line 124 is connected to an outlet port of the dialyzer 126 via a series of blood lines. A blood pump line 128 positioned between the arterial patient line 122 and the dialyzer 126 is operably connected to a peristaltic blood pump 130 extending from the front face of the hemodialysis machine 110.

Figure 7:
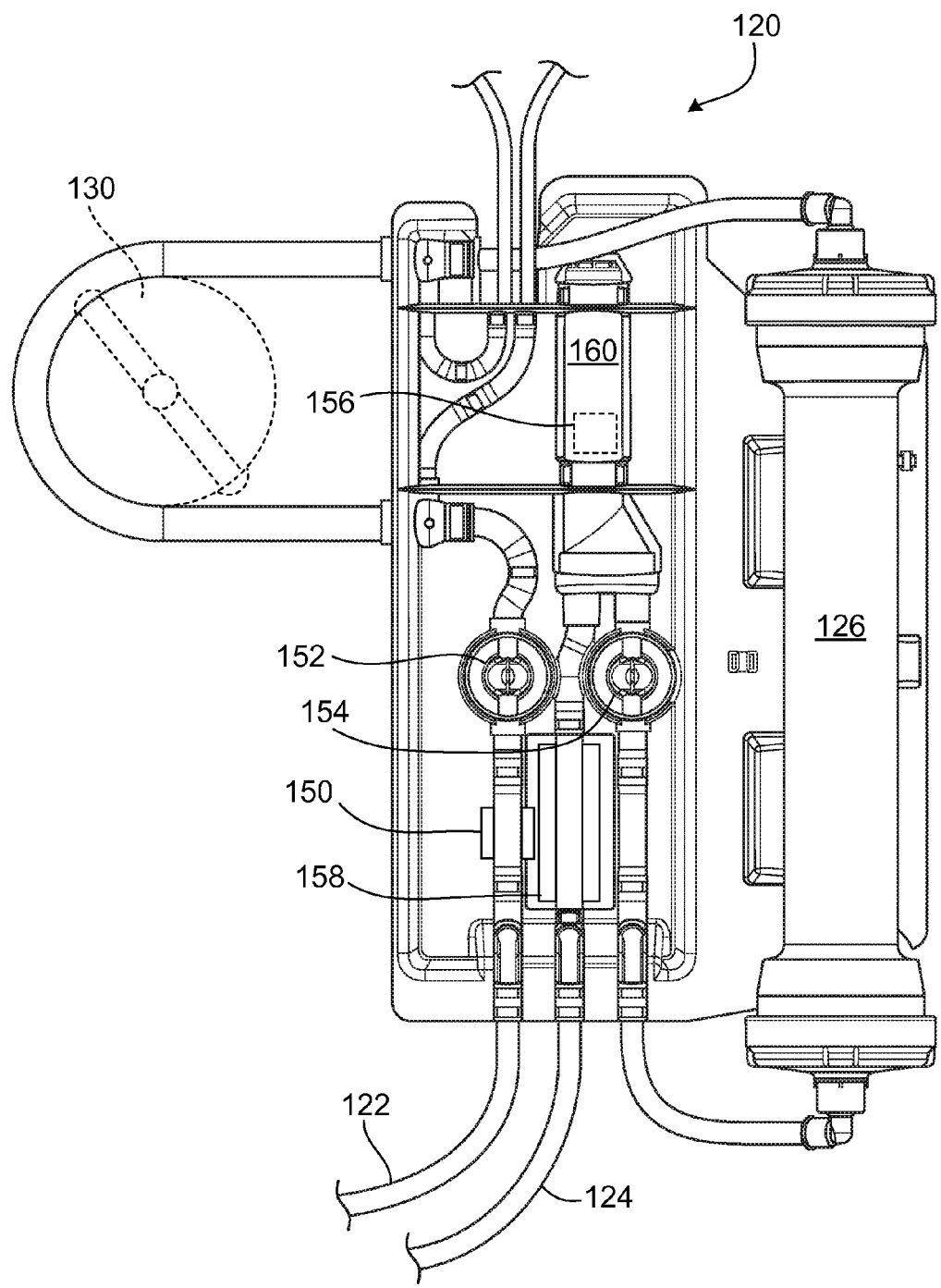
FIG. 7 is a plan view of a blood component set for a hemodialysis system.

The peristaltic blood pump 130 can be operated to pump blood through the various blood lines and components of the blood component set 120. In particular, operation of the blood pump 130 draws blood from the patient through the arterial patient line 122. The blood continues through a series of blood lines and arterial blood components (e.g., sensors) to the dialyzer 126, which separates waste products from the blood. Referring to FIG. 7, the arterial blood components include a blood volume and temperature monitor 150 and an arterial pressure sensor 152. The blood volume and temperature monitor 150 includes an ultrasonic sensor for measuring fluid flow rate through the arterial patient line 122, and a temperature sensor for measuring the temperature of liquid (e.g., blood) flowing through the arterial patient line 122. In some implementations, the fluid flow rate is determined as a function of the measured temperature of the liquid. The arterial pressure sensor 152 monitors the pressure of liquid flowing through the arterial patient line 122.

After passing through the dialyzer 126, the blood flows through a venous pressure sensor 154, which monitors the pressure of liquid flowing through the venous patient line 124, and into an air release chamber 160 in which gas (e.g., air) in the blood can escape before the blood continues to the patient. An ultrasonic level detector 156 is positioned to measure a liquid level in the air release chamber 160.

After leaving the air release chamber 160, the blood is returned to the patient via the venous patient line 124. An integral multi-function sensor 158, such as described above with reference to FIG. 1, is arranged along the venous patient line 124 for monitoring conditions relating to the blood flowing in the venous patient line 124 before it is returned to the patient.

Figure 8:
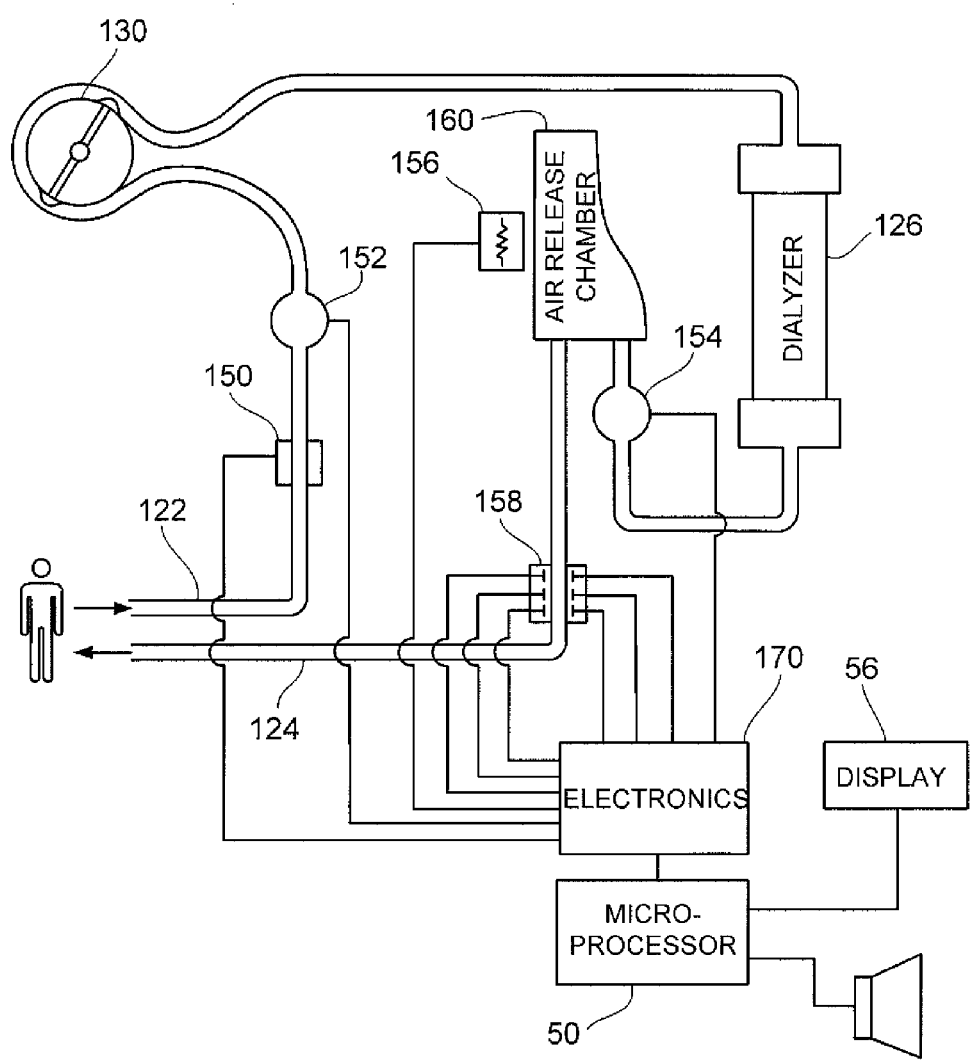
FIG. 8 is a schematic diagram of an extracorporeal fluid circuit for a hemodialysis system.

Referring to FIG. 8, signals from the various sensors (e.g., the blood volume and temperature monitor 150, the arterial and venous pressure sensors 152, 154, the ultrasonic level detector 156, and the integral multi-function sensor 158) can be delivered a microprocessor 50 via associated electronics 170 for processing. The associated electronics 170 include a multiplexer, an analog to digital (A/D) converter, and other associated circuits and components, such as described above with reference to FIG. 3, that provide for communication between the various sensors and the microprocessor 50. The microprocessor 50 and the associated electronics 170 may be enclosed within a housing 102 (FIG. 1) of the hemodialysis machine 110. The microprocessor 50 is in communication with a visual display device 56 of the hemodialysis machine 110, and can use the information obtained from the various sensors to display measurement results, or provide visual warnings on the visual display device 56. The microprocessor 50 can also produce outputs to other devices such as an audible alarm, heating and/or cooling devices within the hemodialysis machine 110 used for controlling the temperature of the dialysate, and/or the peristaltic blood pump 130.

Methods of Operation

During hemodialysis treatment, the integral multi-function sensor 158 is used to sense the presence of air bubbles and/or particles present in blood flowing in the venous patient line 124 via the piezoelectric elements 26a, 26b (FIG. 1). The microprocessor 50 can be configured to halt operation of the peristaltic blood pump 130 if air bubbles and/or particles are detected in the blood flow to inhibit the air bubbles and/or particles from being delivered back to the patient. Alternatively or additionally, the microprocessor 50 can activate a visual or audible alarm if air bubbles and/or particles are detected to inform the machine operator of the condition so that the operator can take appropriate corrective action, such as by manually turning off the peristaltic blood pump 130 and/or disconnecting the patient from the hemodialysis machine 110.

The integral multi-function sensor 158 can also be used to sense a type of liquid in the venous patient line 124, such as blood and saline, and/or to sense an occlusion in the blood flow during use via the optical elements 32, 34 (FIG. 1). Information regarding the detected type of liquid can be displayed and/or an audible alarm can be sounded to provide an indication of the type of liquid detected. The microprocessor 50 can also be configured to automatically halt operation of the peristaltic blood pump 130 and/or activate a visual or audible alarm if an occlusion in the blood flow is detected so that the machine operator can take appropriate corrective action, such as by adjusting the blood lines, manually halting operation of the peristaltic blood pump 130 and/or disconnecting the patient from the hemodialysis machine 110.

The integral multi-function sensor 158 may also be used to sense an occlusion in the blood flow or failure of the peristaltic blood pump 130 by way of the force sensor 30 (FIG. 1). In this regard, changes in the measured pressure of the blood flow within the venous patient line 124 are used to infer the presence of an occlusion or pump failure. Pressure measurements from the force sensor 30 can also be used to detect whether the venous patient line is correctly seated within the sensing slot 12 of the integral multi-function sensor 158 and whether or not liquid (blood) is flowing within the venous patient line 124. The microprocessor 50 can be configured to automatically halt operation of the peristaltic blood pump 130 and/or activate a visual or audible alarm if an occlusion in the blood flow is detected so that the machine operator can take appropriate corrective action, such as by adjusting the blood lines, manually halting operation of the peristaltic blood pump 130 and/or disconnecting the patient from the hemodialysis machine 110. The microprocessor 50 can also be configured to activate an audible or visual alarm if a pump failure is detected, or to indicate whether or not the venous patient line 124 is correctly seated in the integral multi-function sensor 158, and/or to provide an indication of whether or not liquid is flowing within the venous patient line 124 based on signals received from the force sensor 30.

The integral multi-function sensor 158 can also be used to monitor the temperature of blood flowing in the venous patient line 124 via the temperature sensor element 28 (FIG. 1). The measured value of the blood temperature can be used for control purposes, such as turning on and off heating and cooling elements or to advise the machine operator of changes in the blood temperature. For example, the measured temperature can be used to adjust a temperature of dialysate flowing through the dialyzer 126. It may be beneficial to adjust the temperature of the dialysate to match that of the blood flow, so that the dialysate does not substantially affect the temperature of the blood flow as the blood flow passes through the dialyzer 126. In this regard, the microprocessor 50 can use the measured blood flow temperature to control one or more resistive heaters within the hemodialysis machine 110 in order to adjust the temperature of dialysate flowing within the machine 110.

The temperature data measured with the integral multi-function sensor 158 can also be used for recirculation measurement. Recirculation is a condition in which blood that is thought to have been returned to the patient's blood stream via the venous patient line passes back to arterial patient line without traveling through the cardio pulmonary system. To help detect recirculation, the microprocessor 50 can be configured to heat a bolus of dialysate, via control of one or more heating devices (e.g., resistive heaters) of the hemodialysis machine 110, to a temperature above that of the blood flow. This heated bolus of dialysate will, in turn, heat a bolus of the blood as it flows through the dialyzer 126. The temperature sensor element 28 of the integral multi-function sensor 158 can then be used to measure the temperature of the heated bolus of blood before it is returned to the patient (i.e., while it is still in the venous patient line 124). This measured temperature data is then compared to the blood flow temperature measured by the blood volume and temperature monitor 150 in the arterial patient line 122 to determine whether recirculation is present.

If recirculation is not present, then the heated bolus of blood will travel through the patients blood stream, through the cardio pulmonary system, and dissipate a substantial amount of the excess heat before it again reaches the arterial patient line 122, and the blood volume and temperature monitor 150 in the arterial patient line 122 will not detect the heated bolus. On the other hand, if recirculation is present, the heated bolus of blood will reach the arterial patient line 122 without having had sufficient time to dissipate the excess heat, and, as a result, the blood volume and temperature monitor 150 will detect the heated bolus of blood.

The microprocessor 50 can be configured to turn down the blood flow rate, via operation of the peristaltic blood pump 130, and/or provide a visual or audible alarm if recirculation is detected.

While certain systems have been described above, other types of systems can be used to measure or detect characteristics related to flowing fluid. Examples of some such systems are described in U.S. application Ser. No. 11/703,025, filed on Feb. 6, 2007, which is incorporated by reference in its entirety herein.

Specific features are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the patented scope of the appended claims.

What is claimed is:

1. A dialysis system, comprising:
    a dialysis machine;
    a tube connected to the dialysis machine;
    a sensor system, comprising
        a head having a slot configured to receive the tube; and
        a plurality of sensors secured to the head adjacent the slot,
        wherein the plurality of sensors comprise:
            a light emitting element configured to transmit light through the tube when the tube is disposed in the slot;
            a light receiving element configured to receive the light emitted by the light emitting element after the light passes through the tube, and
            an infrared temperature sensor element configured to project infrared energy into the tube when the tube is disposed in the slot,
        wherein the sensor system further comprises a temperature sensing circuit responsive to infrared energy sensed by the infrared temperature sensor element to determine a temperature of fluid in the tube;
    a resistive heater; and
    a microprocessor in communication with the plurality of sensors, wherein the microprocessor is configured to activate the resistive heater to adjust a temperature of dialysate flowing through a dialyzer of the dialysis system based on a temperature of fluid in the tube determined by the temperature sensing circuit,
    wherein fluid in the tube is blood, the tube is a venous line, and the dialysis system further comprises an arterial line and a second temperature sensor configured to measure a temperature of blood flowing through the arterial line, and
    wherein the microprocessor is configured to control the resistive heater in a manner to heat a bolus of dialysate to a temperature greater than a temperature of blood flowing through the dialysis system in order to heat blood flowing through the dialyzer, and to compare a temperature of blood in the arterial line as detected by the second temperature sensor to a temperature of blood in the venous line as detected by the infrared temperature sensor to determine whether recirculation is present.

2. The dialysis system of claim 1, wherein the tube comprises a plurality of tubular segments connected together.

3. The dialysis system of claim 1, wherein the tube is connected to a patient in a manner such that fluid can be drawn from the patient via the tube.

4. The dialysis system of claim 1, wherein the tube is connected to a patient in a manner such that fluid can be delivered to the patient via the tube.

5. The dialysis system of claim 1, wherein the sensor system further comprises a liquid type detection circuit responsive to the light received by the light receiving element to determine the color of fluid in the tube.

6. The dialysis system of claim 5, wherein the liquid type detection circuit also operates to determine whether the tube is present in the slot.

7. The dialysis system of claim 5, wherein the liquid type detection circuit also operates to determine whether liquid is in the tube.

8. The dialysis system of claim 5, wherein the sensor system further comprises a multiplexer controlled by timing signals to separately actuate the liquid type circuit and a circuit associated with at least one of the other sensors.

9. The dialysis system of claim 1, wherein at least one of the plurality of sensors comprises:
    a first piezoelectric element mounted on a first wall of the head adjacent the slot; and
    a second piezoelectric element mounted on a second wall of the head adjacent the slot, the second wall being opposite the first wall.

10. The dialysis system of claim 9, wherein, when the tube is disposed in the slot of the head, the first piezoelectric element and the second piezoelectric element are positioned outside of the tube and are configured to detect an air bubble in fluid in the tube.

11. The dialysis system of claim 10, wherein the sensor system further comprises an air bubble detection circuit to supply ultrasonic energy to one of the piezoelectric sensor elements, to receive the ultrasonic energy transmitted through the tube by the other of the piezoelectric sensor elements, and to determine from the received energy whether an air bubble is present in fluid in the tube.

12. The dialysis system of claim 1, wherein at least one of the plurality of sensors is a force sensor.

13. The dialysis system of claim 12, wherein the sensor system further comprises a force detection circuit to determine a force applied to the force sensor by the tube.

14. The dialysis system of claim 13, wherein the force detection circuit is configured to determine whether the tube is present in the slot.

15. The dialysis system of claim 13, wherein the force detection circuit is configured to determine an internal pressure of the tube.

16. The dialysis system of claim 12, wherein the force sensor contacts an outer surface of the tube when the tube is disposed in the slot.

17. The dialysis system of claim 1, wherein walls of the head adjacent the slot define recesses in which the plurality of sensors are disposed.

18. The dialysis system of claim 17, wherein the walls of the head further define passages extending from the recesses to outer surfaces of the walls, and wires connected to the sensors extend through the passages to a location external the head.

19. The dialysis system of claim 1, wherein the slot has a width that is less than a width of the tube when the tube is undeformed.

20. The dialysis system of claim 1, wherein the head of the sensor system is made of a transparent plastic material.

21. The dialysis system of claim 1, wherein the dialysis machine is a hemodialysis machine.

22. The dialysis system of claim 1, wherein the microprocessor is configured to activate an alarm based on signals from the sensors.

23. The dialysis system of claim 1, further comprising a display device in communication with the microprocessor, wherein the microprocessor is configured to drive the display device to display measurement results based on signals received from the sensors.

24. The dialysis system of claim 1, further comprising a display device, wherein the microprocessor is configured to drive the display device to display warnings based on signals received from the sensors.

25. The dialysis system of claim 1, further comprising a blood pump in communication with the microprocessor, wherein the microprocessor is configured to control operation of the blood pump based on signals received from the sensors.

26. The dialysis system of claim 1, wherein the microprocessor is configured to adjust the temperature of the dialysate flowing through the dialyzer to match the temperature of the fluid in the tube.

27. The dialysis system of claim 1, wherein the fluid in the tube is blood and the tube is connected to the dialyzer such that the blood flows through the dialyzer along with the dialysate.

28. The dialysis system of claim 1, wherein the microprocessor is configured to determine that recirculation is present if the second temperature detects a bolus of blood having an elevated temperature, as compared to other blood flowing through the venous line.

29. The dialysis system of claim 1, wherein the microprocessor is configured to lower a blood flow rate through the dialysis system if recirculation is determined to be present.

30. The dialysis system of claim 1, wherein the microprocessor is configured to activate an alarm of the dialysis system if recirculation is determined to be present.

* * * * *

UNITED STATES PATENT AND TRADEMARK OFFICE
CERTIFICATE OF CORRECTION

PATENT NO. : 8,631,683 B2
APPLICATION NO. : 12/647820
DATED : January 21, 2014
INVENTOR(S) : Naim Dam, Martin Joseph Crnkovich and Roland Levin It is certified that error appears in the above-identified patent and that said Letters Patent is hereby corrected as shown below:

On the Title Page, column 2 Item (57) (Abstract), delete "trough" and insert --through--.

On Title Page 2, column 2 Item (56) (Other Publications), delete "Pimer" and insert --Primer--.

Signed and Sealed this
Twenty-ninth Day of April, 2014

Michelle K. Lee
*Deputy Director of the United States Patent and Trademark Office*